United States Patent
Hoekstra et al.

(10) Patent No.: US 7,405,303 B2
(45) Date of Patent: Jul. 29, 2008

(54) SUBSTITUTED QUINOLINE COMPOUNDS FOR USE AS SELECTIVE ESTROGEN RECEPTOR MODULATOR

(75) Inventors: William Joel Hoekstra, Durham, NC (US); Aaron Bayne Miller, Durham, NC (US); William John Zuercher, Durham, NC (US); Harikrishna Suryakant Patel, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/598,246

(22) PCT Filed: Feb. 22, 2005

(86) PCT No.: PCT/US2005/005467

§ 371 (c)(1),
(2), (4) Date: Aug. 22, 2006

(87) PCT Pub. No.: WO2005/082857

PCT Pub. Date: Sep. 9, 2005

(65) Prior Publication Data

US 2007/0203180 A1   Aug. 30, 2007

Related U.S. Application Data

(60) Provisional application No. 60/547,544, filed on Feb. 25, 2004.

(51) Int. Cl.
*C07D 215/00* (2006.01)
*A61K 31/4709* (2006.01)

(52) U.S. Cl. ...................................... 546/173; 514/312
(58) Field of Classification Search ................ 546/173; 514/312

See application file for complete search history.

(56) References Cited

FOREIGN PATENT DOCUMENTS

DE          3101544 A1 * 8/1982
WO     WO-02/094788 A    11/2002

* cited by examiner

*Primary Examiner*—Rita Desai
*Assistant Examiner*—John Mabry
(74) *Attorney, Agent, or Firm*—J. Scott Young

(57) ABSTRACT

The present invention relates to novel compounds of formula (I) with a variety of therapeutic uses, more particularly novel substituted quinoline compounds particularly useful for selective estrogen receptor modulation.

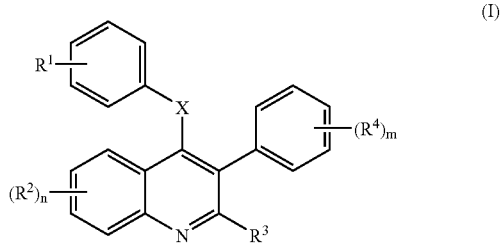

14 Claims, No Drawings

SUBSTITUTED QUINOLINE COMPOUNDS FOR USE AS SELECTIVE ESTROGEN RECEPTOR MODULATOR

CROSS-REFERENCE TO RELATED APPLICATIONS

This application is filed pursuant to 35 USC 371 as a United States National Phase Application of International Patent Application Serial No. PCT/U2005/005467 filed on Feb. 22, 2005, which claims priority from 60/547,544 filed on Feb. 25, 2004 in the United States.

FIELD OF THE INVENTION

The present invention relates to novel compounds with a variety of therapeutic uses, more particularly novel substituted quinoline compounds particularly useful for selective estrogen receptor modulation.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. The most widely accepted hypothesis of how estrogens exert their effects is by binding to an intracellular steroid hormone receptor. After the receptor and bound ligand are transferred to the nucleus of the cell, the complex binds to recognition sites in DNA, which allows for the modulation of certain genes. Additionally, it is now becoming apparent that estrogens may mediate their effects via membrane-initiated signaling cascade, though much of this work is still experimental. Kousteni et al., *Journal of Clinical Investigation*, (2003), 111, 1651-1664, herein incorporated by reference with regard to such teaching.

Certain substances have demonstrated the ability to exhibit their biological activity in a "tissue-selective" manner. In other words, tissue selectivity allows functionality as estrogen agonists in certain tissues, while acting as estrogen antagonists in other tissues. The term "selective estrogen receptor modulators" (SERMs) has been given to these molecules. Examples of SERMs include tamoxifen, raloxifene, lasofoxifene, clomiphene, and nafoxidine. The molecular basis for this tissue-selective activity is not completely understood. Without being limited to any particular theory, the ability of the ligand to place the estrogen receptor into different conformational states and allowing for differential capabilities in recruiting coactivator and corepressor proteins, as well as other important proteins involved in transcriptional regulation, is believed to play a role. See, McDonnell, D. P., *The Molecular Pharmacology of SERMs*, Trends Endocrinol. Metab. 1999, 301-311, herein incorporated by reference with regard to such description.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930, each herein incorporated by reference with regard to such subtype. ERβ is expressed in humans. See, Mosselman et al., *ERβ: Identification and Characterization of a Novel Human Estrogen Receptor*, FEBS Lett., 1996, pp. 49-53, herein incorporated by reference with regard to such expression. The discovery of this second subtype of estrogen receptor significantly increased the biological complexity of estrogen signaling and may be responsible for some of the tissue-selective actions of the currently available SERMs.

As noted above, estrogens have important effects in many non-reproductive tissues. Thus, estrogen modulation is believed useful in the treatment or prophylaxis of diseases and conditions associated with such tissues, including bone, liver, and the central nervous system.

For example, osteoporosis is characterized by the net loss of bone mass per unit volume. Such bone loss results in a failure of the skeleton to provide adequate structural support for the body, thereby creating an increased risk of fracture. One of the most common types of osteoporosis is postmenopausal osteoporosis, which is associated with accelerated bone loss subsequent to cessation of menses and declining levels of endogenous estrogen in women. There is an inverse relationship between densitometric measures of bone mass and fracture risk, for per- and postmenopausal women in the process of rapid bone loss due to declining levels of estrogen. See, Slemenda, et al., *Predictors of Bone Mass in Perimenopausal Women, A Prospective Study of Clinical Data Using Photon Absorptiometry*, Ann. Intern. Med., 1990, pp. 96-101 and Marshall, et al., *Meta-Analysis of How Well Measures of Bone Mineral Density Predict Occurrence of Osteoporotic Fractures*, Br. Med. J., 1996, pp. 1254-1259, each of which is herein incorporated by reference with regard to such relationship. Elderly women currently have a lifetime risk of fractures of about 75%. In addition there is an approximate 40% risk of hip fracture for Caucasian women over age 50 in the United States. The economic burden from osteoporotic fractures is considerable because of the necessity of hospitalization. In addition, although osteoporosis is generally not thought of as life-threatening, the mortality within 4 months of hip fracture is currently approximately 20 to 30%. Current therapies for postmenopausal osteoporosis include hormone replacement therapy or treatment with other antiresorptive agents such as bisphosphonates or calcitonin. Similarly, SERMS have been shown to be effective in the treatment of postmenopausal osteoporosis (see, Lindsay, R.: *Sex steroids in the pathogenesis and prevention of osteoporosis*. In: Osteoporosis 1988. Etiology, Diagnosis and Management. Riggs BL (ed)I, Raven Press, New York, USA (1988):333-358; Barzel US: *Estrogens in the prevention and treatment of postmenopausal osteoporosis*: a review. Am J. Med (1988) 85:847-850; and Ettinger, B., Black, D. M., et al., *Reduction of Vertebral Fracture Risk in Postmenopausal Women with Osteoporosis Treated with Raloxifene*, JAMA, 1999, 282, 637-645, each of which is incorporated by reference with regard to such teaching).

As another example, the effects of estrogens on breast tissue, particularly breast cancer, have been well documented. For example, a previously identified SERM, tamoxifen, decreases the risk of recurrent breast cancer, contralateral breast cancer, and mortality as well as increases the disease-free survival rate of patients with breast cancer at multiple stages of the disease. See, Cosman, F., Lindsay, R. *Selective Estrogen Receptor Modulators: Clinical Spectrum*, Endocrine Rev., 1999, pp. 418-434, herein incorporated by reference with regard to such teaching. The profile of tamoxifen, however, is not ideal due to potential interactive properties on reproductive tissues, such as uterine tissues. There is room for an improved therapy for the treatment of such cancers, namely a SERM with no agonist properties on any reproductive tissues.

Cardiovascular disease is the leading cause of death among postmenopausal women. Until recently, the preponderance of data suggested that estrogen replacement therapy in postmenopausal women reduced the risk of cardiovascular disease, although some studies reported no beneficial effect on overall mortality. See, Barrett-Connor, E. et al., *The Potential of SERMs for Reducing the Risk of Coronary Heart Disease*, Trends Endocrinol. Metab., 1999, pp. 320-325, herein incorporated by reference. The mechanism(s) by which estrogens were believed to exert their beneficial effects on the cardiovascular system are not entirely clear. Potentially estrogen's effects on serum cholesterol and lipoproteins, antioxidant properties, vascular smooth muscle proliferation, and inhibition of arterial cholesterol accumulation were believed to play a role. Id. See also, Cosman, F., Lindsay, R. *Selective Estrogen Receptor Modulators: Clinical Spectrum*, Endocrine Rev., 1999, pp. 418-434, herein incorporated by reference. In light of the recent reports of the HERS II and WHI studies, however, continuous combined Hormone Therapy, namely, CEE+MPA [Conjugated Equine Estrogen+Medroxy Progesterone Acetate], confers no cardiovascular benefit in menopausal women. See, Hulley S., Grady, D., Bush, T., et al., *Randomized trial of estrogen plus progestin for secondary prevention of coronary heart disease in postmenopausal women*. Heart and Estrogen/progestin Replacement Study (HERS) Research Group. J. Am. Med. Assoc. (1998) 280: 605-613 and Wassertheil-Smoller S., Hendrix, S. L., Limacher, M., et al., for the WHI Investigators. *Effect of estrogen plus progestin on stroke in postmenopausal women: the Women's Health Initiative: a randomized trial*. JAMA (2003) 289, 2673-2684, each herein incorporated by reference with regard to such teaching. To what extent these findings may be extrapolated to SERMs is an issue that remains to be determined.

Other therapeutic alternatives include estrogen replacement therapy and/or hormone replacement therapy ("HRT"), which may be useful in the treatment of vasomotor symptoms, genitourinary atrophy, depression, and diabetes. Over 75% of women experience vasomotor symptoms during the climacteric years. Clinical signs, such as vasomotor symptoms and genitourinary atrophy, abate upon treatment with estrogen replacement therapy. Sagraves, R., *J. Clin. Pharmacol*. (1995), 35(9 Suppl):2S-10S, herein incorporated by reference with regard to such teaching. Preliminary data suggest that estradiol may alleviate depression during perimenopause and that the combination of estrogens and selective serotonin reuptake inhibitors may alleviate depression during the postmenopausal period. Soares, C. N., Poitras, J. R., and Prouty, J., *Drugs Aging*, (2003), 20(2), 85-100, herein incorporated by reference with regard to such teaching. Furthermore, hormone replacement therapy may improve glycemic control among women with diabetes. Palin, S. L. et al., *Diabetes Research and Clinical Practice*, (2001), 54, 67-77; Ferrara, A. et al., *Diabetes Care*, (2001), 24(7), 1144-1150), each incorporated herein by reference with regard to such teaching. There is a need, however, for improved therapies that present better side effect profiles as compared to HRT.

The present inventors discovered novel compounds that bind to and modulate estrogen receptor alpha ("ER-α") and estrogen receptor beta ("ER-β"). Thus, as a SERM, these compounds are believed to be useful for the treatment and/or prophylaxis of, without limitation, menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

SUMMARY OF THE INVENTION

The present invention includes compounds of Formula I:

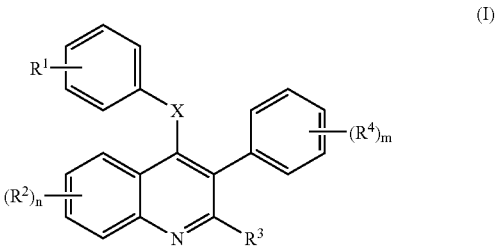

(I)

including salts, solvates, and pharmaceutically acceptable derivatives thereof wherein $R^1$ is —CH=CH—$R^5$;
$R^5$ is —CN, —C(O)OH, —C(O)—N($R^6$)($R^7$);
$R^6$ and $R^7$ each independently are hydrogen, alkyl, aryl; or
$R^6$ and $R^7$ may combine with the nitrogen atom to which they are attached to form a 3 to 7 membered ring, where said ring may be optionally substituted;

each $R^2$ independently is hydrogen, halogen, haloalkyl, hydroxy, alkoxy, aryloxy, aralkyloxy, alkoxycarbonyloxy, aryloxycarbonyloxy, aralkyloxycarbonyloxy, alkylsulfonyloxy, arylsulfonyloxy, aralkylsulfonyloxy, or acyloxy;

n is 1 or 2;

$R^3$ is hydrogen, hydroxy, alkyl, alkoxy, aryloxy, aralkyloxy, haloalkylsulfonyloxy, halogen, haloalkyl, aryl, heteroaryl, aralkyl, or heteroaralkyl;

X is —O—, —S—, —S(O)—, or —S(O)$_2$—;

each $R^4$ independently is hydrogen, halogen, haloalkyl, hydroxy, alkoxy, aryloxy, aralkyloxy, alkoxycarbonyloxy, aryloxycarbonyloxy, aralkyloxycarbonyloxy, alkylsulfonyloxy, arylsulfonyloxy, aralkylsulfonyloxy, or acyloxy; and m is 1 or 2.

In one embodiment $R^5$ is —C(O)OH and, thus, the present invention also includes pharmaceutically acceptable ester derivatives, for example where $R^5$ is —C(O)O$R^8$ and $R^8$ is alkyl or aralkyl.

Preferably $R^5$ is —C(O)OH, —C(O)NH$_2$, —C(O)NH(alkyl), —C(O)N(alkyl)$_2$, —C(O)-piperidinyl, or —CN.

Preferably X is O or S. More preferably X is O.

In one embodiment n is 1 and $R^2$ is hydroxyl, alkoxy, or aralkyloxy. Preferably $R^2$ is hydroxy substituted on the 7 position of the depicted quinoline ring.

Preferably $R^3$ is alkyl, hydroxyl, aralkyloxy, haloalkylsulfonyloxy, or aryl. More preferably $R^3$ is $C_1$-$C_6$ alkyl or phenyl. Still further, $R^3$ is ethyl.

In one embodiment m is 1 and $R^4$ is hydrogen. In one embodiment m is 1 and $R^4$ is haloalkyl. Preferably, $R^4$ is —CF$_3$ and is substituted in the 3 position on the depicted phenyl ring.

Particular compounds of the present invention include:
4-[(7-Hydroxy-2-ethyl-3-phenyl-4-quinolinyl)oxyphenyl]-2-propenoic acid;
4-[(7-Hydroxy-2-ethyl-3-phenyl-4-quinolinyl)oxyphenyl]-2-propenoamide;
4-[(7-Hydroxy-2-ethyl-3-phenyl-4-quinolinyl)oxyphenyl]-2-propeno-N-isopropylamide;
4-[(7-Hydroxy-2-ethyl-3-phenyl-4-quinolinyl)oxyphenyl]-2-propeno-N,N-dimethylamide;

4-[(7-Hydroxy-2-ethyl-3-phenyl-4-quinolinyl)oxyphenyl]-2-propeno-N-piperidineamide;
4-[(7-Hydroxy-2-ethyl-3-phenyl-4-quinolinyl)oxyphenyl]-2-propenonitrile;
4-[(7-Hydroxy-2-ethyl-3-(3-trifluoromethylphenyl)-4-quinolinyl)oxyphenyl]-2-propeno-N-isopropylamide;
4-[(7-Hydroxy-2-ethyl-3-(3-trifluoromethylphenyl)-4-quinolinyl)oxyphenyl]-2-propenoic acid;
4-[(7-Hydroxy-2-phenyl-3-phenyl-4-quinolinyl)oxyphenyl]-2-propenoic acid;
3-[(7-Hydroxy-2-ethyl-3-phenyl-4-quinolinyl)oxyphenyl]-2-propenoic acid; and
4-[(7-Hydroxy-2-ethyl-3-phenyl-4-quinolinyl)thiophenyl]-2-propenoamide.

One aspect of the present invention includes a compound substantially as herein above described with reference to any one of the Examples.

Another aspect of the present invention is a pharmaceutical composition that includes a compound of the present invention. Preferably any pharmaceutical composition also includes a pharmaceutically acceptable excipient, carrier, diluent, or mixture thereof.

Another aspect of the present invention is a compound as herein described for use in the prophylaxis or treatment of diseases, disorders, conditions, or side effects that respond to selective estrogen receptor modulation. Preferably a compound as herein described may be for use in the prophylaxis or treatment of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium. Preferably the use relates to menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and/or osteoporosis. osteoporosis, cardiovascular disease, breast cancer, uterine cancer, prostate cancer, dyslipidemia, menopausal vasomotor conditions, central nervous system conditions and disorders, prostate hyperplasia, urinary incontinence, atherosclerosis, uterine fibroid disease, aortic smooth muscle cell proliferation, or endometriosis.

Another aspect of the present invention is the use of a compound as herein described in the manufacture of a medicament for use in the prophylaxis or treatment of diseases, disorders, conditions, or side effects that respond to selective estrogen receptor modulation. For example, the use of a compound in the manufacture of a medicament may relate to the prophylaxis or treatment of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium. Preferably the disease, disorder, condition, or side effect is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and/or osteoporosis. osteoporosis, cardiovascular disease, breast cancer, uterine cancer, prostate cancer, dyslipidemia, menopausal vasomotor conditions, central nervous system conditions and disorders, prostate hyperplasia, urinary incontinence, artherosclerosis, uterine fibroid disease, aortic smooth muscle cell proliferation, or endometriosis.

Another aspect of the present invention includes a method of eliciting a biological or medical response of a tissue, system, animal, or human that responds to selective estrogen receptor modulation in mammals comprising administering to said tissue, system, animal, or human in need of such treatment an effective amount of a compound as herein described. Preferably includes a therapeutically effective amount of a compound as herein described. Further, the prophylaxis or treatment relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, or reperfusion damage of ischemic myocardium in a mammal. More preferably the disease, disorder, condition, or side effect is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and/or osteoporosis. osteoporosis, cardiovascular disease, breast cancer, uterine cancer, prostate cancer, dyslipidemia, menopausal vasomotor conditions, central nervous system conditions and disorders, prostate hyperplasia, urinary incontinence, artherosclerosis, uterine fibroid disease, aortic smooth muscle cell proliferation, or endometriosis.

DETAILED DESCRIPTION OF THE PREFERRED EMBODIMENT

The present invention is described in terms known and appreciated by those skilled in the art. For ease of reference certain terms hereafter are defined. The fact that certain terms are defined, however, should not be considered as indicative that defined terms are used in a manner necessarily inconsistent with the ordinary meaning or, alternatively, that any term that is undefined is indefinite or not used within the ordinary meaning. Rather, all terms used herein are believed to describe the invention such that one of ordinary skill can appreciate the scope of the present invention.

The term "alkyl", alone or in combination with any other term, refers to a straight-chain or branched-chain saturated aliphatic hydrocarbon radical containing if so specified, a preferred number of carbon atoms. As used herein, an alkyl group optionally may be further substituted. Exemplary optional substituents include alkyl, cycloalkyl, haloalkyl, alkoxy, hydroxy, amino optionally substituted by alkyl, carboxy, carbamoyl optionally substituted by alkyl, acyl, nitro, halogen, haloalkyl, heterocyclyl, heteroaryl, aryl, heteroaralkyl, or aralkyl. Examples of "alkyl" as used herein include, but are not limited to, methyl, ethyl, propyl, isopropyl, isobutyl, n-butyl, tert-butyl, isopentyl, n-pentyl, and the like.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like, for example —$CF_3$.

As used herein the term "alkoxy" refers to the group —$OR_a$, where $R_a$ is alkyl as herein defined, for example, methoxy and the like.

As used herein the term "aryloxy" refers to the group —$OR_a$, where $R_a$ is aryl or heteroaryl as herein defined, for example, phenoxy and the like.

As used herein the term "aralkyloxy" refers to the group —$OR_a$, where $R_a$ is aralkyl or heteroaralkyl as herein defined, for example, benzyloxy and the like.

As used herein the term "acyl" refers to an organic radical obtained by dropping the hydroxyl from an associated acid group. Thus, the term includes the group —$C(O)R_a$, where $R_a$ is hydrogen, alkyl, aryl, aralkyl, heteroaryl, heteroaralkyl, heterocyclyl, or heterocyclylalkyl as each is herein defined.

As used herein the term "acyloxy" refers to groups such as:

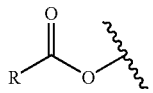

where the R is alkyl, aryl, heteroaryl, or heterocyclyl, as each is defined herein.

As used herein the term "alkoxycarbonyloxy" refers to groups such as:

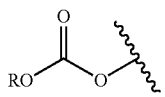

where R represents an alkyl group as herein defined.

As used herein the term "aryloxycarbonyloxy" refers to groups such as:

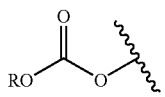

where R represents an aryl or heteroaryl group as herein defined.

As used herein the term "aralkyloxycarbonyloxy" refers to groups such as:

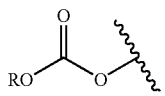

where R represents an aralkyl or heteroaralkyl group as herein defined.

As used herein the term "alkylsulfonyloxy" refers to groups such as:

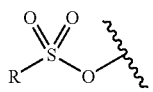

where R represents an alkyl group as herein defined.

As used herein the term "arylsulfonyloxy" refers to groups such as:

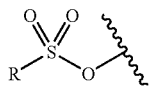

where R represents an aryl or heteroaryl group as herein defined.

As used herein the term "aralkylsulfonyloxy" refers to groups such as:

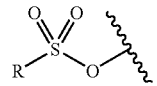

where R represents an aralkyl or heteroaralkyl group as herein defined.

As used herein the term "hydroxy" refers to the group —OH.

The term "aryl", alone or in combination with any other term, refers to an optionally substituted aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl are, but are not limited to, phenyl, naphthyl, indenyl, azulenyl, fluorenyl, anthracenyl, phenanthrenyl, tetrahydronaphthyl, indanyl, phenanthridinyl and the like. Exemplary optional substituents include alkyl, aryl, aralkyl, heteroaryl, heteroaralkyl, cycloalkyl, heterocyclyl, halogen, haloalkyl, carboxy, carbamoyl, acyl, nitro, hydroxy, alkoxy, aryloxy, aralkyloxy, acyloxy, nitro, amino, and substituted amino. Multiple degrees of substitution should be considered as included within the present invention.

The term "aralkyl" further refers to groups of —$R_aR_b$, where $R_a$ is an alkylene group and $R_b$ is an aryl. As used herein, the term "alkylene" refers to a straight or branched chain divalent hydrocarbon radical, preferably having from one to ten carbon atoms. Alkylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and lower perfluoroalkyl. Multiple degrees of substitution are allowed. Examples of alkylene groups include, but are not limited to, methylene and the like. Examples of aralkyl groups include, but are not limited to, benzyl and the like.

The term "heteroaryl", alone or in combination with any other term, refers to an optionally substituted aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls. Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl. Exemplary optional substituents include alkyl, aryl, aralkyl, heteroaryl, heteroaralkyl, cycloalkyl, heterocyclyl, halogen, haloalkyl, carboxy, carbamoyl, acyl, nitro, hydroxy, alkoxy, aryloxy, aralkyloxy, acyloxy, nitro, amino, and substituted amino. Multiple degrees of substitution should be considered as included within the present invention. Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroaralkyl" further refers to groups of —$R_aR_b$, where $R_a$ is an alkylene as defined herein and $R_b$ is a heteroaryl as defined herein.

The term "heteroatom" means nitrogen, oxygen, or sulfur and includes any oxidized form of nitrogen, such as N(O), {$N^+$—$O^-$}, and oxidized forms of sulfur such as S(O) and $S(O)_2$, as well as the quaternized form of any basic nitrogen.

Also, as used herein throughout the present specification, the phrase "optionally substituted" or variations thereof denote an optional substitution, including multiple degrees of substitution, with one or more substitutent group. The phrase should not be interpreted as duplicative of the substitutions herein described and depicted.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are also within the scope of this invention.

Certain compounds of this invention may exist in alternative tautomeric forms. All such tautomeric forms of the present compounds are within the scope of the invention. Unless otherwise indicated, the representation of either tautomer is meant to include the other.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "derivative" refers to any, but preferably pharmaceutically acceptable, derivative of a compound of the present invention. Preferably, upon administration to a mammal, a derivative of the present invention is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition. Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. For example, an effective amount of a compound of formula (i) for the treatment of humans suffering from osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein that are mediated by estrogen.

Pharmaceutical formulations may be presented in unit dose forms containing a predetermined amount of active ingredient per unit dose. Such a unit may contain, as a non-limiting example, 0.5 mg to 1 g of a compound of the formula (i), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders, such as carboxymethylcellulose, aliginates, gelatins, or polyvinyl pyrrolidone, solution retardants, such as paraffin, resorption accelerators such as a quaternary salt and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone (PVP), pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring agents.

The compounds of the present invention and their salts, solvates, and physiologically functional derivatives thereof, may be employed alone or in combination with other therapeutic agents for the treatment of the conditions herein described. For example, in osteoporosis therapy, combination with other osteoporosis therapeutic agents is envisaged. Osteoporosis combination therapies according to the present invention thus comprise the administration of at least one compound of formula (I) or a salt, solvate, or physiologically functional derivative thereof, and the use of at least one other osteoporosis treatment method. Preferably, combination therapies according to the present invention comprise the administration of at least one compound of formula (I) or a salt, solvate, or physiologically functional derivative thereof, and at least one other osteoporosis treatment agent, for example, a bone building agent. The compound(s) of formula (I) and the other pharmaceutically active agent(s) may be administered together or separately and, when administered separately, administration may occur simultaneously or sequentially in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other osteoporosis treatment agents may be in combination by administration concomitantly in: (1) a unitary pharmaceutical composition including each compound; or (2) separate pharmaceutical compositions each including one of the compounds. Alternatively, the combination may be administered separately in a sequential manner wherein one treatment agent is administered first and the other(s) subsequently or vice versa. Such sequential administration may be close in time or remote in time.

The compounds of the present invention and their salts, solvates, and physiologically functional derivatives thereof, may be employed alone or in combination with other therapeutic agents for the treatment of the conditions herein described. For example, regarding the use of the compounds of the present invention in the prevention of reduced bone mass, density, or growth, combination may be had with other anabolic or osteoporosis therapeutic agents. As one example, osteoporosis combination therapies according to the present invention would thus comprise the administration of at least one compound of the present invention or a salt, solvate, or physiologically functional derivative thereof, and the use of at least one other osteoporosis therapy. As a further example, combination therapies according to the present invention include the administration of at least one compound of the present invention or a salt, solvate, or physiologically functional derivative thereof, and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) and the agent(s) and the relative timings of administration will be selected in order to achieve the desired combined therapeutic effect. The administration in combination of a compound of the present invention including salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

As noted, one potential additional osteoporosis treatment agent is a bone building (anabolic) agent. Bone building agents can lead to increases in parameters such as bone mineral density that are greater than those than can be achieved with anti-resorptive agents. In some cases, such anabolic agents can increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-ardenergic agonists, serotonin 5-HT$_D$ agonists, selective serotonin reuptake inhibitors, agents that inhibit somatostatin or its release, 5-α-reductase inhibitors, aromatase inhibitors, GnRH inhibitors, parathyroid hormone, bisphosphonates, estrogen, testosterone, SERMs, progesterone receptor agonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis, bone demineralization and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondro- dysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, reperfusion damage of ischemic myocardium, In particular, the compounds of the present invention are believed useful, either alone or in combination with other agents, in the treatment of menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

The compounds of this invention may be made by a variety of methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

ABBREVIATIONS

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

| | |
|---|---|
| g (grams); | mg (milligrams); |
| L (liters); | ml (milliliters); |
| μL (microliters); | psi (pounds per square inch); |
| M (molar); | mM (millimolar); |
| Hz (Hertz); | MHz (megahertz); |
| mol (mol(s)); | mmol (millimol(s)); |
| RT (room temperature); | |
| min (minutes); | h (hours); |
| mp (melting point); | TLC (thin layer chromatography); |
| $T_r$ (retention time); | RP (reverse phase); |
| TEA (triethylamine); | TFA (trifluoroacetic acid); |
| TFAA (trifluoroacetic anhydride); | THF (tetrahydrofuran); |
| $CDCl_3$ (deuterated chloroform); | $CD_3OD$ (deuterated methanol); |
| $SiO_2$ (silica); | $BCl_3$ (boron chloride); |
| $H_2O_2$ (hydrogen peroxide); | $H_2SO_4$ (sulfuric acid); |
| DMSO (dimethylsulfoxide); | EtOAc (ethyl acetate); |
| HCl (hydrochloric acid); | $CH_2Cl_2$ (ethylene chloride); |
| $LiAlH_4$ (lithium aluminum hydride); | $CHCl_3$ (chloroform); |
| DME (1,2-dimethoxyethane); | DMF (N,N-dimethylformamide); |
| HOAc (acetic acid); | BOC (tert-butyloxycarbonyl); |
| n-BuLi (n-butyl lithium); | LiOH (lithium hydroxide); |
| Ac (acetyl); | atm (atmosphere); |
| TBS (t-butyldimethylsilyl); | DMAP (4-dimethylaminopyridine); |
| $NaHCO_3$ (sodium bicarbonate); | Me (methyl); |
| Et (ethyl); | EtOH (ethanol); |
| MeOH (methanol); | DMAc (dimethyl acetamide) |
| tBu (tert-butyl); | $PtO_2$ (platinum dioxide). |

Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Compounds were analyzed on a Micromass Quattro Micro QAA075 LC/MS using either Conditions I or Conditions II (below). Retention times were recorded for each compound.

Conditions I: The column was a Synergi Max-RP, 50×2.0 mm, 4-micron column 85% $H_2O$, 15% MeOH to 100% MeOH in 4 minutes, holding at 100% MeOH for final 2 minutes. Water contains 0.1% v/v formic acid, MeOH contains 0.075% v/v Formic Acid. The flow rate was 0.8 ml/min with 3 uL of solution injected. Mass spectra were recorded on a Micromass Quattro Micro utilizing electrospray ionization switching between positive and negative modes with DAD scanning from 220 to 400 nm.

Conditions II (GW870541X): The column was a Synergi Hydro-RP 50×2.0 mm, 4 micron column 98% $H_2O$, 2% MeOH to 100% MeOH in 4 minutes, holding at 100% MeOH for final 2 minutes. Water contains 0.1% v/v formic acid, MeOH contains 0.075% v/v Formic Acid. The flow rate was 0.8 ml/min with 3 uL of solution injected. Mass spectra were recorded on a Micromass Quattro Micro utilizing electrospray ionization switching between positive and negative modes with DAD scanning from 220 to 400 nm.

Compounds were purified on an Agilent 1100 HPLC using a Phenomenex Luna C-18(2), 150×21.2 mm, 5 micron column; a linear gradient of 10-90% ACN/$H_2O$/0.1% TFA was run over 10 minutes, followed by a 4 minute organic wash. The flow rate was 20 mL/min with DAD at 254 nm.

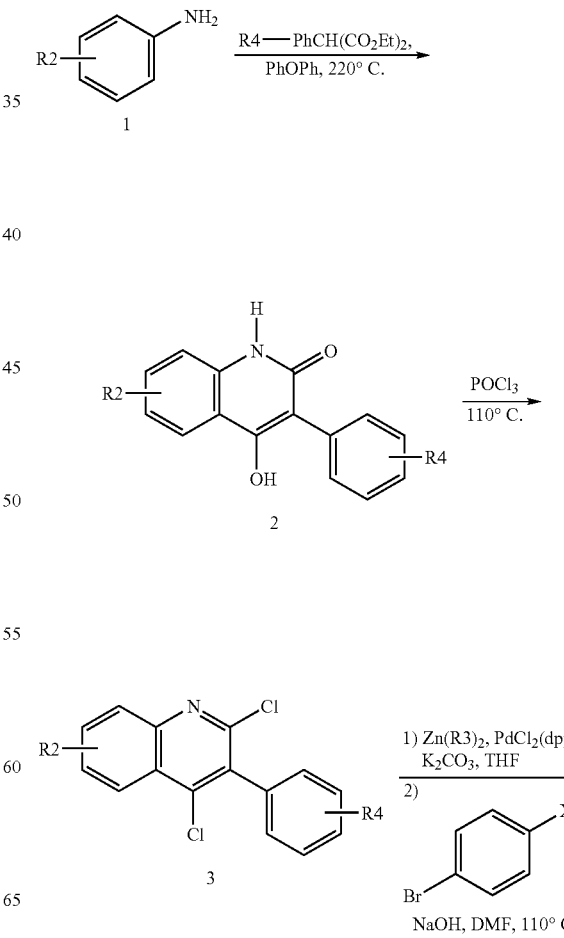

Scheme 1

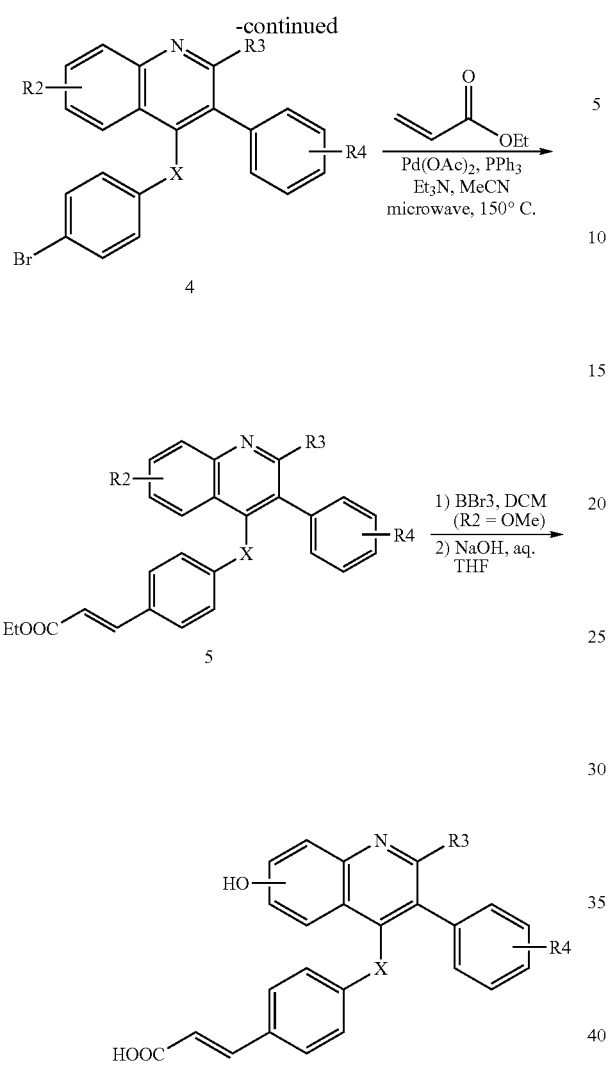

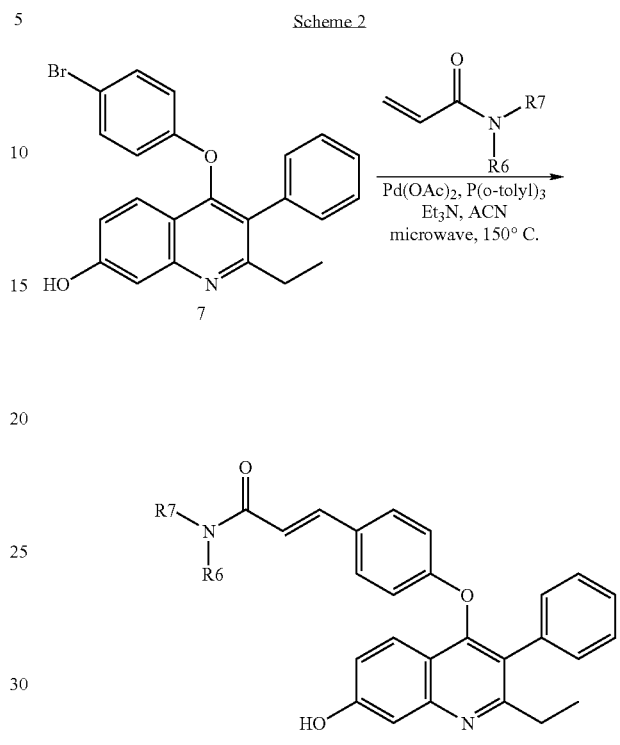

EXAMPLES

Example 1

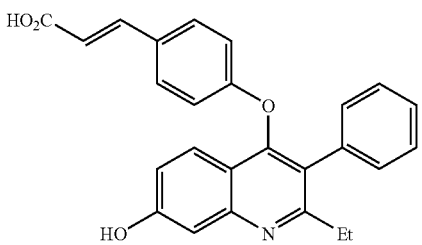

4-[(7-Hydroxy-2-ethyl-3-phenyl-4-quinolinyl)oxyphenyl]-2-propenoic acid (6a; R2=7-OH, R3=Et, R4=H in Scheme 1)

A. 3-Phenyl-4-hydroxy-7-methoxyquinol-2-one (2a)

Compounds of formula (I) can be prepared starting from anilines 1 (Scheme I). The requisite anilines were condensed with aryl substituted dialkyl malonates at elevated temperature to afford quinolones 2. Conversion of 2 to dichloroquinolines 3 in phosphorous oxychloride followed by Negishi coupling of (R³)₂Zn and displacement with bromophenols or bromothiophenols afforded tetracyclic intermediates 4. Heck coupling of 4 with ethyl acrylate furnished 5. For compounds wherein R²=OMe, the methyl ether may be unmasked with boron tribromide to provide alcohol products. For acrylic acid products, the corresponding esters were saponified with sodium hydroxide to give products such as 6.

Acrylamide products related to 6 were prepared according to the representative example as follows. Aryl bromides 4 were de-methylated using boron tribromide conditions shown in Scheme 1 to give the corresponding hydroxyquinoline 7, and the hydroxyquinoline 7 was coupled with variably substituted acrylamide reagents using Heck conditions [(Pd(OAc)₂, triethylamine, acetonitrile, microwave irradiation at 150° C.] to furnish acrylamide products 8 (Scheme 2):

A dark solution of 3-anisidine (5.37 g, 44.8 mmol), diethyl 2-phenylmalonate (10.57 g, 44.8 mmol), and diphenyl ether (50 mL) was heated at 220° C. for 1 h without a reflux condenser to allow ethanol evaporation. The reaction was cooled to rt, and the resultant gray precipitate filtered and washed with diethyl ether and dried to afford 11.0 g 2a (R2=7-OMe in Scheme 1, 92% yield): MS (M+H)$^+$ 269.28.

B. 2,4-Dichoro-3-phenyl-7-methoxyquinoline (3a)

A slurry of 2a (7.0 g, 26.2 mmol) and phosphorous oxychloride (30 mL) was heated at 110° C. for 2 h, cooled to rt, and stored in the refrigerator for 1 h. The resultant mixture was slowly decanted into ice cold 10% potassium carbonate (50 mL) to furnish a white precipitate. The ppt was filtered and partitioned between 10% potassium carbonate (100 mL) and EtOAc (150 mL). This mixture was stirred for 1 h, filtered, and the resultant white powder dried to afford 3a (7.3 g, 91% yield): MS (M+H)$^+$ 304.02.

C. 2-Ethyl-3-phenyl-4-(4-bromophenyloxy)-7-methoxyquinoline (4a)

To a solution of 3a (2.99 g, 9.83 mmol), potassium carbonate (4.076 g, 29.49 mmol) and dichloro[1,1'-bis(diphenylphosphino)ferrocene]palladium (i) dichloromethane adduct (0.80 g, 0.98 mmol) in THF (60 mL) was added diethylzinc (10 mL of 1.0M hexanes, 10.0 mmol). The reaction was heated to reflux for 6 h, then cooled to ambient temperature and evaporated. The reaction was poured into a saturated NH$_4$Cl solution (50 mL) and extracted with EtOAc (3×40 ml). The combined organic layer was washed with brine (50 mL) and dried over MgSO4, and evaporated. The crude solid was purified over silica gel-60 via medium pressure liquid chromatography (MPLC; EtOAc/hexanes) to afford 2.64 g (91% yield) of a yellow solid. $^1$H NMR (300 MHz, DMSO-d$_6$): δ 8.10-8.07 (s, 1H), 7.57-7.45 (m, 4H), 7.38-7.34 (m, 3H), 3.96 (s, 3H), 2.67-2.60 (q, 2H), 1.16-1.11 (t, 3H). MS (M+H)$^+$ 298.07.

A pyrex screw cap tube (25×200 mm) was charged with the yellow solid (1.18 g, 3.97 mmol), sodium hydroxide (0.794 g, 19.85 mmol) and 4-bromophenol (1.37 g, 7.94 mmol) in DMF (10 mL). The reaction was heated to 110° C. for 24 h, then cooled to ambient temperature. The reaction was poured in to water (20 mL) and extracted with EtOAc (3×20 ml). The combined organic layer was washed with brine (40 mL) and dried over MgSO4, and evaporated. The crude solid was purified over silica gel-60 via medium pressure liquid chromatography (MPLC; EtOAc/hexanes) to afford 0.898 g (52% yield) of an off white solid (4a). $^1$H NMR (300 MHz, DMSO-d$_6$):δ7.76-7.73 (d, 1H), 7.49 (s, 1H), 7.33-7.28 (m, 3H), 7.22-7.19 (d, 2H), 7.16-7.10 (m, 3H), 6.50-6.47 (d, 2H), 3.99 (s, 3H), 2.85-2.78 (q, 2H), 1.25-1.20 (t, 3H). MS (M+H)$^+$ 434.07.

D. Ethyl 4-[(7-methoxy-2-ethyl-3-phenyl-4-quinolinyl)oxyphenyl]-2-propenoate (5a)

A CEM microwave tube was charged with 4a (0.750 g, 1.73 mmol), triphenylphosphine (0.243 g, 0.80 mmol), palladium acetate (0.097 g, 0.43 mmol), ethyl acrylate (0.56 mL, 5.18 mmol) and triethylamine (0.73 mL, 5.18 mmol) in ACN (5 mL). The reaction was subjected to microwaves (150 w, 30 min 150° C.). The reaction was evaporated and poured into water (10 mL) and extracted with EtOAc (3×10 ml). The combined organic layers were washed with brine (20 mL) and dried over MgSO4, and evaporated. The crude solid was purified over silica gel-60 via medium pressure liquid chromatography (MPLC; EtOAc/hexanes) to afford 0.59 g (76% yield) of a yellow solid. $^1$H NMR (300 MHz, CDCl$_3$): δ7.74-7.71 (d, 1H), 7.58-7.53 (d, 1H), 7.49-7.48 (d, 1H), 7.28-7.25 (m, 3H), 7.16-7.07 (m, 3H), 6.61-6.58 (d, 2H), 6.28-6.22 (d, 1H), 4.26-4.19 (q, 4H), 3.95 (s, 3H), 2.85-2.77 (q, 2H), 1.33-1.28 (t, 3H), 1.24-1.19 (t, 3H). MS (M+H)$^+$ 454.19.

E. 4-[(7-Hydroxy-2-ethyl-3-phenyl-4-quinolinyl) oxyphenyl]-2-propenoic acid (6a, Example 1)

A solution of 5a (0.300 g, 0.65 mmol), in DCM (10 mL) was cooled to −20° C. in a MeOH/ice bath. Under nitrogen, BBr$_3$, was added slowly (6 mL of 1.0M DCM, 6.0 mmol). After 3 h the reaction was warmed to ambient temperature (3 h), and quenched with MeOH (20 mL). The reaction was evaporated, quenched with MeOH (20 mL) and evaporated to afford a crude solid. A solution of this crude solid in THF (5 mL) was transferred to a pyrex tube (16×125 mm) and NaOH (10.0 mL of 1.0M H$_2$O, 10.0 mmol) was added. The reaction was heated to 50° C. for 18 h. The reaction was evaporated and poured into water (10 mL) and adjusted to pH 2 with 1.0N HCl, and extracted with EtOAc (3×5 ml). The combined organic layer was washed with brine (20 mL) and dried over MgSO4, and evaporated. The crude solid was purified over silica gel-60 via medium pressure liquid chromatography (MPLC; EtOAc/hexanes) to afford 0.043 g (16% yield over 2 steps) of a yellow solid (6a). $^1$H NMR (300 MHz, DMSO-d$_6$): δ7.59-7.49 (m, 3H), 7.44 (s, H), 7.36-7.25 (m, 6H), 7.09-7.06 (m, 1H), 6.72-6.69 (d, 2H), 6.36-6.31 (d, 1H), 2.71-2.63 (q, 2H), 1.17-1.12 (t, 3H). MS (M+H)$^+$ 412.15. C26H21NO4.

Example 2

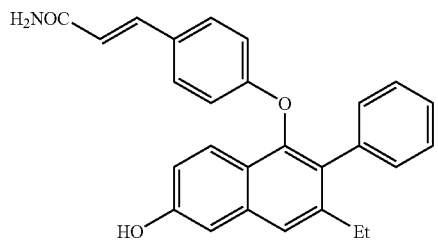

4-[(7-Hydroxy-2-ethyl-3-phenyl-4-quinolinyl)oxyphenyl]-2-propenoamide (8a, Example 2)

A CEM microwave tube was charged with 7 (0.040 g, 0.095 mmol), triphenylphosphine (0.0137 g, 0.045 mmol), palladium acetate (0.005 g, 0.024 mmol), acrylamide (0.032 g, 0.46 mmol) and triethylamine (0.0387 mL, 0.29 mmol) in ACN (2 mL). The reaction was subjected to microwaves (150 w, 30 min 175° C.). The reaction was filtered, evaporated and poured into water (3 mL) and extracted with EtOAc (3×5 ml). The combined organic layer was washed with brine (5 mL) and dried over MgSO4, and evaporated. The crude solid was purified via high pressure liquid chromatography (HPLC; ACN/H$_2$O) to afford 0.021 g (54% yield) of a yellow solid. $^1$H NMR (300 MHz, CD$_3$OD): δ7.75-7.72 (d, 1H), 7.40-7.29 (m, 7H), 7.22-7.18 (m, 2H), 7.12-7.08 (dd, 2H), 6.65-6.62 (d, 2H), 6.49-6.44 (d, 1H), 2.82-2.75 (q, 2H), 1.18-1.13 (t, 3H). MS (M+H)$^+$ 411.16. C26H22N2O3.

Example 3

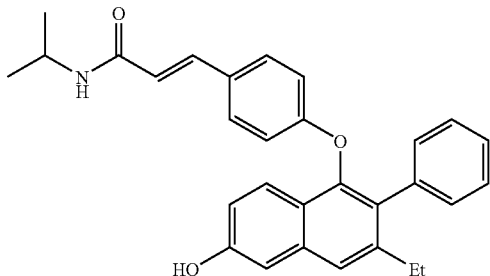

4-[(7-Hydroxy-2-ethyl-3-phenyl-4-quinolinyl)oxyphenyl]-2-propeno-N-isopropylamide (Example 3)

Example 3 (0.0253 g) was prepared as described for Example 2: LC/MS rt 4.19 min (Conditions I); MS (M+H)$^+$ 453.55. C29H28N2O3.

Example 4

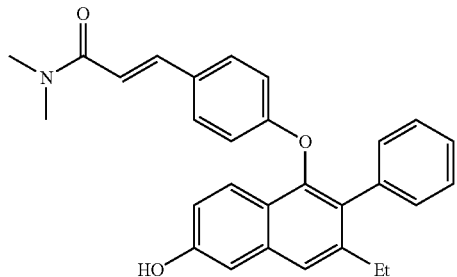

4-[(7-Hydroxy-2-ethyl-3-phenyl-4-quinolinyl)oxyphenyl]-2-propeno-N,N-dimethylamide (Example 4)

Example 4 (0.0174 g) was prepared as described for Example 2: LC/MS rt 3.45 min (Conditions II); MS (M+H)$^+$ 439.52. C28H26N2O3.

Example 5

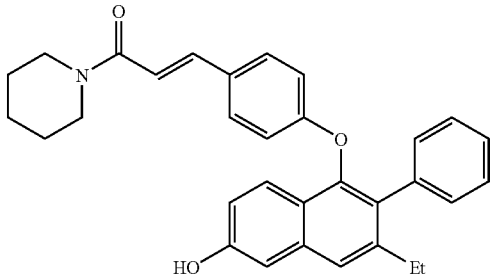

4-[(7-Hydroxy-2-ethyl-3-phenyl-4-quinolinyl)oxyphenyl]-2-propeno-N-piperidineamide (Example 5)

Example 5 (0.0268 g) was prepared as described for Example 2: LC/MS rt 3.77 min (Conditions I); MS (M+H)$^+$ 479.58. $C_{31}H_{30}N2O3$.

Example 6

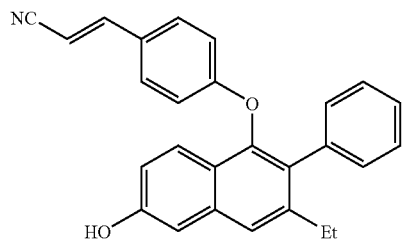

4-[(7-Hydroxy-2-ethyl-3-phenyl-4-quinolinyl)oxyphenyl]-2-propenonitrile (Example 6)

Example 6 (0.0253 g) was prepared as described for Example 2: LC/MS rt 3.59 min (Conditions I); MS (M+H)$^+$ 393.46. C26H20N2O2

Example 7

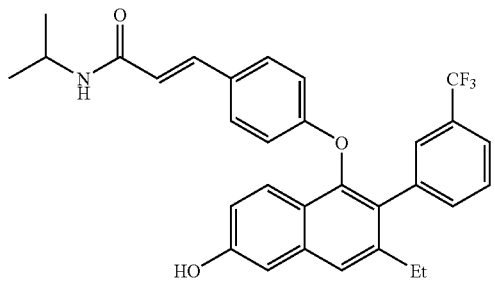

4-[(7-Hydroxy-2-ethyl-3-(3-trifluoromethylphenyl]-4-quinolinyl)oxyphenyl]-2-propeno-N-isopropylamide (Example 7)

Example 7 (0.0141 g) was prepared as described for Example 2: LC/MS rt 3.96 min (Conditions I); MS (M+H)$^+$ 521.20. C30H27F3N2O3.

Example 8

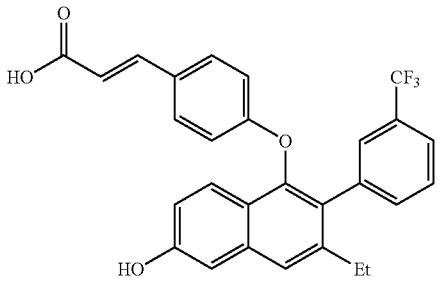

4-[(7-Hydroxy-2-ethyl-3-(3-trifluoromethylphenyl)-4-quinolinyl)oxyphenyl]-2-propenoic acid (Example 8)

Example 8 (0.0167 g) was prepared as described for Example 1: LC/MS rt 3.93 min (Conditions I); MS (M+H)$^+$ 480.45. C27H2OF3NO4.

Example 9

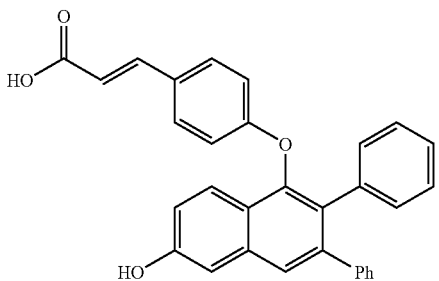

4-[(7-Hydroxy-2-phenyl-3-phenyl-4-quinolinyl)oxyphenyl]-2-propenoic acid (Example 9)

Example 9 (0.0446 g) was prepared as described for Example 1: LC/MS rt 4.10 min (Conditions I); MS (M+H)$^+$ 460.51. C30H21NO4.

Example 10

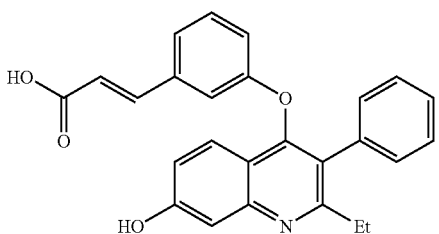

3-[(7-Hydroxy-2-ethyl-3-phenyl-4-quinolinyl)oxyphenyl]-2-propenoic acid (Example 10)

Example 10 (0.009 g) was prepared as described for Example 2 from 3-bromophenol and intermediate 3: LC/MS rt 3.43 min (Conditions I); MS (M+H)$^+$ 412.56. C26H21NO4.

Example 11

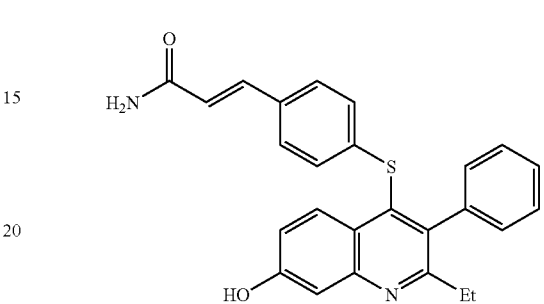

4-[(7-Hydroxy-2-ethyl-3-phenyl-4-quinolinyl)thiophenyl]-2-propenoamide (Example 11)

Example 11 (0.016 g) was prepared as described for Example 2: LC/MS rt 3.31 min (Conditions I); MS (M+H)$^+$ 428.12. C26H21NO2S.

BIOLOGICAL DATA

Protein Preparation:

The ligand binding domain of both ERα and ERβ were sub-cloned into pGEX-2T vector which had been modified to contain KpnI and BamHI restriction sites in the multiple cloning region. GST-hERα and GST-hERβ proteins were made by transforming BL21 (DE3)pLYS S competent cells with the appropriate expression plasmid. Liquid cultures containing standard Luria-Bertani (LB) broth with 0.1 mg/ml ampicillin and 0.033 mg/ml chloramphenicol were grown at 37° C. to an OD600 of 0.5-1.0 then induced with IPTG for 2-3 hours. The cells were collected by centrifugation and resuspended in lysis buffer (50 mM Tris pH 7.9; 250 mM KCl; 1% Triton X-100; 10 mM DTT; 1 mM PMSF). The lysate was then placed on dry ice until completely frozen The frozen lysate was thawed and centrifuged 20 min at 4° C. at 80K rpm in a TLA 100.2 rotor in a Beckman TL-100 ultracentrifuge. The supernatant was retained and glycerol was added to a final concentration of 10%. The protein content of the supernatant was quantitated using the BioRad Protein Assay Reagent. The protein was then stored at −80° C. until used in the binding assay.

Competition Binding Assay:

Polylysine coated Yttrium Silicate SPA beads (Amersham #RPNQ 0010) are resuspended in assay buffer [10 mM potassium phosphate buffer pH 7.0 containing 2 mM EDTA, 50 mM NaCl, 1 mM DTT, 2 mM CHAPS, 10% glycerol] to a concentration of 1 g/60 ml. 30 ul (0.5 mg) of the SPA beads are then added to each well of a Packard OptiPlate (Packard 6005190, Packard Instruments, Meriden, Conn.). The ERα or ERβ protein is diluted to the appropriate concentration (empirically determined for each protein prep by generating a protein curve using 0.5 to 10 ug total protein and 1 nM

[3H]Estradiol and selecting a protein concentration that does not deplete the radioligand) and added as 30 ul aliquots to each well. [2,4,6,7,16,17-3H(N)]-Estradiol is added as a 30 ul aliquot to give a final assay concentration of 1 nM. To give a final volume of 100 ul, either 10 ul of a test compound solution (typically in 10% DMSO as solvent), solvent containing no test compound (to determine total binding, T), or solvent containing 17-b-estradiol at 100 uM (to determine non-specific binding, NS) are finally added to the plate. The plates are shaken vigorously for two hours then counted on a Packard TopCount using the protocol for counting tritium yttrium silicate SPA beads. Data analysis was done by standard methods. % Bound was calculated for each concentration of each test compound using the equation % Bound=100*((Test−NS)/(T−NS)). % Bound was plotted vs concentration and curve fitting was accomplished using non-linear regression.

Saturation Binding Assay:

Saturation binding assays were run similarly to competition assays. Dissociation constants (Kd) were determined by generating twelve-point saturation curves using 10 uM 17-b-estradiol to define nonspecific binding. [2,4,6,7,16,17-3H(N)]-estradiol was added such that the final concentration ranged from 0.1 to 100 nM.

| Example # | Estrogen Receptor Binding[a] | |
|---|---|---|
| | Avg. ER α p$K_i$[b] | Avg. ER β p$K_i$[b] |
| 1 | 6.87 | 7.21 |
| 2 | 7.83 | 7.55 |
| 3 | 8.01 | 7.76 |
| 4 | 7.95 | 7.74 |
| 5 | 7.55 | 7.64 |
| 6 | 7.59 | 7.50 |
| 7 | 7.51 | 7.26 |
| 8 | 7.05 | 6.57 |
| 9 | 5.53 | 6.17 |
| 10 | 5.81 | 5.80 |
| 11 | 5.50 | 5.74 |

[a]Values derived from SPA competition binding assay;
[b]p$K_i$ = −log of the concentration of test compound required to achieve an apparent $K_i$ value (n = 2).

Test compounds are employed in free or salt form.

All research compiled with the principles of laboratory animal care (NIH publication No. 85-23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:
1. A compound of Formula I:

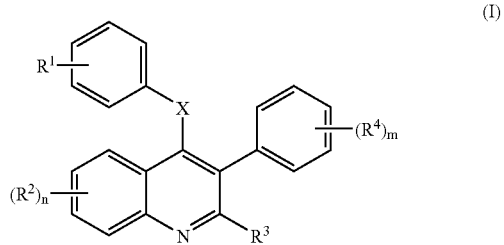

including pharmaceutically acceptable salts wherein
$R^1$ is —CH=CH—$R^5$;
$R^5$ is selected from —CN, —C(O)OH, and —C(O)—N($R^6$)($R^7$);
$R^6$ and $R^7$ each independently are selected from hydrogen and unsubstituted alkyl; or
$R^6$ and $R^7$ combine with the nitrogen atom to which they are attached to form a piperidinyl ring;
each $R^2$ independently is selected from hydrogen, halogen, haloalkyl, hydroxy, and alkoxy;
n is 1 or 2;
$R^3$ is selected from hydrogen, hydroxy, unsubstituted alkyl, alkoxy, phenyl, halogen, and haloalkyl;
X is —O—, —S—, —S(O)—, or —S(O)$_2$—;
each $R^4$ independently is selected from hydrogen, haloalkyl, hydroxy, and alkoxy; and
m is 1 or 2.
2. The compound of claim 1 wherein X is O or S.
3. The compound of claim 2 wherein X is O.
4. The compound of claim 1 wherein n is 1 and $R^2$ is selected from hydroxyl, and alkoxy.
5. The compound of claim 4 wherein $R^2$ is hydroxy substituted on the 7 position of the depicted quinoline ring.
6. The compound of claim 1 wherein $R^3$ is selected from alkyl, hydroxyl, and phenyl.
7. The compound of claim 6 wherein $R_3$ is $C_1$-$C_6$ alkyl or phenyl.
8. The compound of claim 7 wherein $R^3$ is ethyl.
9. The compound of claim 1 wherein m is 1 and $R^4$ is hydrogen.
10. The compound of claim 1 wherein m is 1 and $R^4$ is haloalkyl.
11. The compound of claim 10 wherein $R^4$ is —$CF_3$ and is substituted in the 3 position on the depicted phenyl ring.
12. A compound selected from the group consisting of:
4-[(7-Hydroxy-2-ethyl-3-phenyl-4-quinolinyl)oxyphenyl]-2-propenoic acid;
4-[(7-Hydroxy-2-ethyl-3-phenyl-4-quinolinyl)oxyphenyl]-2-propenoamide;
4-[(7-Hydroxy-2-ethyl-3-phenyl-4-quinolinyl)oxyphenyl]-2-propeno-N-isopropylamide;
4-[(7-Hydroxy-2-ethyl-3-phenyl-4-quinolinyl)oxyphenyl]-2-propeno-N, N-dimethylamide;
4-[(7-Hydroxy-2-ethyl-3-phenyl-4-quinolinyl)oxyphenyl]-2-propeno-N-piperidineamide;
4-[(7-Hydroxy-2-ethyl-3-phenyl-4-quinolinyl)oxyphenyl]-2-propenonitrile;
4-[(7-Hydroxy-2-ethyl-3-(3-trifluoromethylphenyl)-4-quinolinyl)oxyphenyl]-2-propeno -N-isopropylamide;
4-[(7-Hydroxy-2-ethyl-3-(3-trifluoromethylphenyl)-4-quinolinyl)oxyphenyl]-2-propenoic acid;

4-[(7-Hydroxy-2-phenyl-3-phenyl-4-quinolinyl)oxyphenyl]-2-propenoic acid;

3-[(7-Hydroxy-2-ethyl-3-phenyl-4-quinolinyl)oxyphenyl]-2-propenoic acid; and

4-[(7-Hydroxy-2-ethyl-3-phenyl-4-quinolinyl)thiophenyl]-2-propenoamide.

13. A pharmaceutical composition comprising a compound according to claim 1.

14. The pharmaceutical composition of claim 13 further comprising a pharmaceutically acceptable excipient, carrier, diluent, or mixtures thereof.

* * * * *